United States Patent [19]

Nishimura et al.

[11] Patent Number: 4,595,530
[45] Date of Patent: Jun. 17, 1986

[54] THIODEAZAPURINE DERIVATIVES

[75] Inventors: Susumu Nishimura, Chiba; Hiroaki Nomura, Osaka, both of Japan

[73] Assignee: Takeda Chemical Industries, Ltd., Doshomachi, Japan

[21] Appl. No.: 590,357

[22] Filed: Mar. 16, 1984

[30] Foreign Application Priority Data

Mar. 17, 1983 [JP] Japan ................................. 58-45725

[51] Int. Cl.⁴ ................. C07D 223/04; C07D 225/02; C07D 487/04
[52] U.S. Cl. ............................. 260/239 B; 260/243.3; 544/117; 544/280; 514/258
[58] Field of Search .............................. 544/280, 117; 260/239 B, 243.3

[56] References Cited

U.S. PATENT DOCUMENTS 4,435,569 3/1984 Nishimura et al. ................ 544/280

FOREIGN PATENT DOCUMENTS 3036390 5/1982 Fed. Rep. of Germany ...... 544/280
812366 4/1959 United Kingdom ................ 544/280

OTHER PUBLICATIONS

Journal of Biological Chemistry, 254, p. 3067 (1979)—Novel Mechanism of Post-Transcriptional Modification of TRNA—Okada.
Biochemical and Biophysical Research Communications, P96, p. 313 (1980) Administration of Queuine To Mice Relieves Modified Nucleoside Queuosine Deficiency in Ehrlich Ascites Tumor TRNA—Katze.

Primary Examiner—George F. Lesmes
Assistant Examiner—S. A. Gibson
Attorney, Agent, or Firm—Wegner & Bretschneider

[57] ABSTRACT

7-Deazapurine derivatives of the formula:

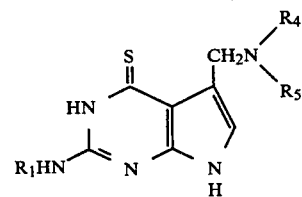

wherein $R_1$ is hydrogen atom or an acyl group and $R_4$ and $R_5$ each is a hydrogen atom or a hydrocarbon residue which may optionally have one or more substituents or $R_4$ and $R_5$, together with the adjacent nitrogen atom, from a cyclic amino group are useful as an antitumor agent, microbicide or disinfectant.

17 Claims, No Drawings

THIODEAZAPURINE DERIVATIVES

This invention relates to novel 7-deazapurine derivatives and a process for production thereof.

Natural 6-oxo-modified bases (for example, Q base, Pre $Q_1$ base) having the same nucleus as that of compounds of this invention are widely distributed in life as constituents of certain tRNA (tRNA$^{Tyr}$, tRNA$^{His}$, tRNA$^{Asp}$ and tRNA$^{Asn}$). These bases are situated at the first position of the anticodons of the aforementioned-tRNAs and play an important biological role by recognizing the genetic information from mRNA directly and being involved in protein synthesis.

With the recent advance of fundamental biochemical research, in particular, the structures of tRNAs and the role they play in vital phenomena have been elucidated one after another and the differences in tRNA between a cancer cell and a normal cell have also been clarified. One of the differences is that in a cancer cell the uptake of Q bases into tRNA precursors is incomplete and there invariably exist Q-deficient tRNAs. It has also been observed that when a Q base is supplied from an external source, such a Q-deficient tRNA takes the Q base into the predetermined position (the first letter of the anticodon) and thereby returns to the normal tRNA and that generally the uptake of Q bases is not observed in normal cells but is specific to cancer cells [Nishimura S., Taisha (Metabolism) Vol. 17, Special Issue [Gann (Cancer) 80], pp. 127-136 (1980)].

Under the circumstances the present inventors studies various derivatives of such 6-oxo-modified bases and found that the compounds obtainable on transformation of the 6-position of such bases to a thio group are novel compounds having excellent antitumor and antibiotic activities. These studies were followed by further studies which led to completion of this invention.

This invention relates to
(1) a 7-deazapurine derivative of the formula:

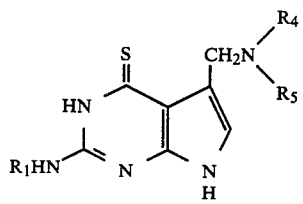

wherein $R_1$ is hydrogen atom or an acyl group, and $R_4$ and $R_5$ each is a hydrogen atom or a hydrocarbon residue which may optionally have one or more substituents or $R_4$ and $R_5$, together with the adjacent nitrogen atom, form a cyclic amino group or a salt thereof, and (2) a method for producing a 7-deazapurine derivative of the formula (I) or a salt thereof, which comprises subjecting a 7-deazapurine derivative of the formula:

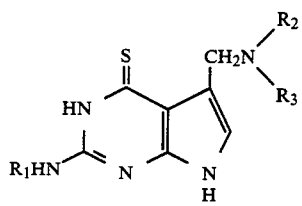

wherein $R_1$ is as defined above and $R_2$ and $R_3$ each is an alkyl, alkenyl or aralkyl group containing a methylene group in the α-position thereof or $R_2$ and $R_3$, together with the adjacent nitrogen atom, form a cyclic amino group, to substitution reaction with an amine of the formula:

wherein $R_4$ and $R_5$ have the same meaning as defined above.

Referring to the above formulae, the acyl groups $R_1$ may be those having the molecular weight of not more than about 400. The examples of the acyl group are alkanoyl, aroyl, and so on. The alkanoyl group preferably has 1 to 18 carbon atoms, and is exemplified by formyl, acetyl, propionyl, butyryl, isobutyryl, valeryl, isovaleryl, pivaloyl, hexanoyl, heptanoyl, octanoyl, 2-ethylhexanoyl, nonanoyl, decanoyl, undecanoyl, tridecanoyl, tetradecanoyl, pentadecanoyl, hexadecanoyl, heptadecanoyl, octadecanoyl, etc. The alkanoyl group having 1 to 10 carbon atoms is preferable among others.

The aroyl group preferably contains 7 to 12 carbon atoms and includes, among others, benzoyl, toluoyl, naphthoyl, etc., and the benzoyl group and the like are preferable among others.

The groups $R_2$ and $R_3$ may be the same group or different groups. Examples of the alkyl group, which has a methylene group in α-position, include groups containing 1 to 10 carbon atoms such as methyl, ethyl, n-propyl, n-butyl, isobutyl, pentyl, isopentyl, hexyl, isohexyl, heptyl, octyl, nonyl, decyl, etc. Particularly preferred are alkyl groups of about 1 to 6 carbon atoms. Examples of the alkenyl group represented by $R_2$ and $R_3$ include groups containing about 3 to 13 carbon atoms such as allyl(2-propenyl), 2-butenyl, 2-pentenyl, 2-hexenyl, 4-propyl-2-pentenyl, cinnamyl, 2-nonyl-2-butenyl, etc. Particularly preferred are alkenyl groups of about 3 to 9 carbon atoms. These alkyl and alkenyl groups may each carry substituent groups in optional substitutable position or positions other than the α-position, and examples of such substituent groups include alkyl groups of about 1 to 4 carbon atoms (e.g. methyl, ethyl, propyl, isopropyl, butyl, isobutyl, sec-butyl, tert-butyl), alkoxy groups of about 1 to 4 carbon atoms (e.g. methoxy, ethoxy, propoxy, iso-propoxy, n-butoxy, iso-butoxy, sec-butoxy, tert-butoxy), alkanoyl groups of about 1 to 4 carbon atoms (e.g. formyl, acetyl, propionyl, n-butyryl, iso-butyryl), hydroxy, nitro, halogen (e.g. fluorine, chlorine, bromine, iodine), carboxy, cyano, trifluoromethyl, dialkylamino (e.g. dimethylamino, diethylamino, dipropylamino, diisopropylamino, dibutylamino), alkanoylamido (e.g. formamido, acetamido, propionylamido, butyrylamido, isobutyrylamido) and so on.

Examples of the aralkyl group represented by $R_2$ or $R_3$ containing a methylene group in the α-position include groups containing about 7 to 12 carbon atoms such as benzyl, phenethyl, 3-phenylpropyl, naphthylmethyl, naphthylethyl, etc. Particularly preferred is benzyl. These aralkyl groups may each carry substituent group or groups in its alkylene moiety other than the α-position and/or its aryl(phenyl) ring, and examples of such substituents include the groups mentioned hereinbefore as examples of the substituent groups of said alkyl and alkenyl groups.

Examples of the cyclic amino group which is formed between $R_2$ and $R_3$ taken together with the adjacent nitrogen atom include cyclic amino groups of 5 or 6 members, and each of the cyclic amino groups may contain a second hetero-atom (e.g. N and/or O) in addition to the adjacent nitrogen atom as a ring member. Specific examples of such cyclic amino groups include 1-pyrrolidinyl, 1-pyrrolinyl, 1-imidazolidinyl, 1-imidazolinyl, 1-pyrazolidinyl, 1-pyrazolinyl, morpholino, piperidino, 1-piperazinyl, etc. These cyclic amino groups may each carry substituent group or groups at any position other than the position (α) adjoining to the nitrogen atom, and examples of such substituent groups include the groups mentioned hereinbefore as examples of the substituent groups of said alkyl and alkenyl groups.

Referring to the above formulae, the hydrocarbon residue of $R_4$ and $R_5$ each may for example be those having the molecular weight of not more than about 400, and exemplified by alkyl, alkenyl, cycloalkyl, cycloalkenyl, aralkyl or aryl group. The alkyl may for example be an alkyl group of 1 to 18 carbon atoms (e.g. methyl, ethyl, propyl, isopropyl, butyl, isobutyl, sec-butyl, tert-butyl, pentyl, isopentyl, hexyl, isohexyl, heptyl, octyl, nonyl, decyl, undecyl, dodecyl, tetradecyl, hexadecyl, octadecyl, 1,2-dimethylpropyl, 1-ethylpropyl, 1,2,2-trimethylpropyl, 1-propylbutyl, 2-ethylhexyl). The alkenyl may for example be an alkenyl group of 2 to 12 carbon atoms (e.g. vinyl, allyl, 1-methylvinyl, 2-methylvinyl, 1-octenyl, 1-decenyl). The cycloalkyl may for example be a cycloalkyl group of 3 to 12 carbon atoms (e.g. cyclopropyl, cyclobutyl, cyclopentyl, cyclohexyl, cycloheptyl, cyclooctyl, adamantyl). The cycloalkenyl may for example be a cycloalkenyl group of 3 to 8 carbon atoms (e.g. cyclopentenyl, cyclohexenyl, cycloheptenyl, cyclooctenyl, cyclopentadienyl, cyclohexadienyl, cycloheptadienyl, cyclooctadineyl). The aralkyl may for example be an aralkyl group of 7 to 13 carbon atoms (e.g. benzyl, α-methylbenzyl, phenetyl, diphenylmethyl). The aryl may for example be an aryl group of 6 to 10 carbon atoms (e.g. phenyl, α-naphthyl, β-naphthyl).

The groups $R_4$ and $R_5$ may taken together with the adjacent nitrogen atom, form a ring. The cyclic group is preferably a 4- to 10-membered ring, such as azetidinyl, pyrrolidinyl, pyrrolinyl, pyrrolyl, imidazolyl, pyrazolyl, imidazolinyl, piperidino, morpholino, dihydropyridyl, tetrahydropyridyl, N-methylpiperazinyl, N-ethylpiperazinyl, azacycloheptyl, azacyclooctyl, isoindolyl, indolyl, indolinyl, 2-isoindolinyl, azacyclononyl, azacyclodecyl, etc.

The hydrocarbon residues $R_4$ and $R_5$ and the cyclic group formed by $R_4$ and $R_5$ as taken together with the adjacent nitrogen atom may be substituted by one to 3 substituents. Examples of such substituents include alkyl groups of 1 to 4 carbon atoms (e.g. methyl, ethyl, propyl, isopropyl, isobutyl, sec-butyl, tert-butyl), alkoxy groups of 1 to 4 carbon atoms (e.g. methoxy, ethoxy, propoxy, iso-propoxy, n-butoxy, iso-butoxy, sec-butoxy, tert-butoxy) which may be substituted by hydroxy, alkanoyl groups of 1 to 4 carbon atoms (e.g. formyl, acetyl, propionyl, n-butyryl, iso-butyryl), alkanoyloxy groups of 1 to 4 carbon atoms (e.g. formyloxy, acetyloxy, propionyloxy, n-butyryloxy, iso-butyryloxy), carboxy, alkoxycarbonyl groups of 2 to 4 carbon atoms (e.g. methoxycarbonyl, ethoxycarbonyl, n-propoxycarbonyl, iso-propoxycarbonyl, n-butoxycarbonyl, isobutoxycarbonyl, t-butoxycarbonyl), halogens (e.g. fluorine, chlorine, bromine, iodine), hydroxy, nitro, cyano, trifluoromethyl, amino, $C_{1-4}$ monoalkylamino (e.g. methylamino, ethylamino, propylamino, isopropylamino, butylamino), carboxymethylamino, di-($C_{1-4}$-alkyl)amino (e.g. dimethylamino, diethylamino, dipropylamino, diisopropylamino, dibutylamino), dicarboxymethylamino, $C_{1-4}$ alkanoylamino (e.g. formamido, acetamido, propionylamido, butylamido, isobutylamido), etc.

It is to be noted that the

group in the formulas (III) and (I) is different from the

group in the compounds of formula (II).

The molecular weight of amine (III) is preferably not more than about 500.

The substitution reaction in accordance with the invention can be effected, for example, by bringing the compound (II) or a salt thereof into contact with the compound (III) or a salt thereof in a (III)/(II) molar ratio of about 1 to 20 in the absence or presence of an adequate solvent at a temperature of about 0° C. to the boiling point of the solvent employed, preferably at a temperature within the range of about 20° to 100° C., for about one hour to about 5 days. In case the compound (II) is used in the form of a quaternary salt, such as a quaternary salt with methyl bromide, methyl iodide, methyl methanesulfonate, methyl benzenesulfonate or methyl p-toluenesulfonate, the reaction can be effected under milder conditions. The quaternary salt of compound (II) prepared in the above case may be subjected to substitution reaction with the compound (III), either after isolation or directly without isolation. Where $R_1$ is an acyl group, deacylation (elimination of $R_1$) may, as necessary, be effected simultaneously by continuing heating of the reaction mixture at about 70° to 100° C. The deacylation may also be conducted by any known method of hydrolysis (e.g. acid hydrolysis, alkali hydrolysis, ammonolysis). The solvent for the substitution reaction between compound (II) and compound (III) is exemplified as water, methanol, ethanol, propanol, butanol, pentanol, tetrahydrofuran, dioxane, acetonitrile, pyridine, dimethylformamide, dimethyl sulfoxide, sulfolane, and adequate mixtures of these. In cases where the compound (II) or compound (III) is used in the form of a salt, the desired product (I) can advantageously be produced by adjusting the reactant mixture to an optimal pH (generally about 5 to 13) with a base (e.g. sodium hydroxide, potassium hydroxide, lithium hydroxide, barium hydroxide, triethylamine, N-methylmorpholine) or a salt (e.g. sodium chloride, potassium chloride, calcium chloride, sodium carbonate, potassium carbonate, sodium hydrogen carbonate).

In cases where the hydrocarbon residues $R_4$ and $R_5$ are substituted, for example, by a carboxy, hydroxy, amino or alkylamino group, a starting compound (III) having such a substituent already protected or protected beforehand (e.g. alkanoyloxy, alkoxycarbonyl, alkanoylamido) by any per se known method [J. F. W. McOmie, Protective Groups in Organic Chemistry, Plenum Press, London and New York (1973)] may, as necessary, be subjected to substitution reaction with another starting compound (II), followed by elimination of the protective group from the resulting compound (I).

The elimination of such protective group is effected by subjecting the protective group-bearing compound to an adequate, generally known protective group elimination reaction. Thus, for instance, an acid (e.g. hydrochloric acid, hydrobromic acid, sulfuric acid, nitric acid, phosphoric acid, acetic acid, trifluoroacetic acid, boron trifluoride, boron tribromide, hydrogen bromide-acetic acid), or a base (e.g. lithium hydroxide, sodium hydroxide, potassium hydroxide, barium hydroxide, potassium carbonate, sodium carbonate, aqueous ammonia, methylamine, dimethylamine, ethylamine, diethylamine, trimethylamine, triethylamine) is added and the mixture is maintained, in an appropriate solvent (e.g. water, methanol, ethanol, propanol, butanol, dioxane, tetrahydrofuran, methyl ether, ethyl ether, dichloromethane, chloroform, carbon tetrachloride, benzene, toluene, xylene, or an adequate mixture of these), at a temperature of about $-15°$ to $100°$ C., preferably $-10°$ to $50°$ C., for about 30 minutes to about 100 hours, preferably for about 1 to 20 hours. Alternatively, a catalyst suited for use in catalytic reduction (e.g. palladium, platinum, rhodium, ruthenium, nickel) is added and catalytic reduction is carried out in an appropriate solvent (e.g. water, methanol, ethanol, propanol, butanol, dioxane, tetrahydrofuran, methyl ether, ethyl ether, benzene, toluene, xylene, ethyl acetate, methyl acetate, acetic acid, or an adequate mixture of these) at a temperature of about $10°$ to $50°$ C. for about 1 to 100 hours.

The 7-deazapurine derivative (I) produced by the method of the invention can be isolated from the reaction mixture by generally known separation and/or purification methods, such as concentration, solvent extraction, chromatography, and recrystallization. The compound (I), when obtained in the free form, may be converted to a pharmaceutically acceptable salt by the conventional method.

The salts of the compound (I) are exemplified by mineral acid salts with hydrochloric acid, sulfuric acid, nitric acid, phosphoric acid, boric acid, etc., organic acid salts with oxalic acid, tartaric acid, acetic acid, trifluoroacetic acid, methanesulfonic acid, benzensulfonic acid, p-toluenesulfonic acid, camphorsulfonic acid, etc., and quaternary salts with methyl bromide, methyl iodide, methyl methanesulfonate, methyl benzenesulfonate, methyl p-toluensulfonate, etc.

The compound (I), when obtained in a salt form other than the quaternary salt form, may, as desired, be converted to the free form. In this instance, the conversion to the free form can easily be effected by subjecting the salt of compound (I) to an adequate, generally known treatment, such as neutralization or anion exchange chromatography.

The thus-obtained compounds (I) and salts thereof inhibit the growth of cultured L5178Y cells in vitro and of Meth A, Sarcoma 180 and so forth in vivo and thus have antitumor activity. The compounds (I) or salts thereof, when intraperitoneally administered to mice in a dose of 200 mg/kg, do not cause any death. Therefore, the compounds (I) and salts thereof can be used as antitumor agents for the tumor treatment in warm-blooded animals, especially mammals (e.g. mouse, rat, cat, dog, rabbit, etc.).

In using as antitumor agents, they may be administered orally or parenterally either as they are or in the powder, granule, tablet, capsule, suppository or injection form, for instance, which can be prepared in the conventional manner by using pharmacologically acceptable carriers, excipients, diluents and so forth. The dose depends on the animal to be treated, the condition and severity of the disease, the kind of the compound, the route of administration and other factors, and generally amounts to about 10 to 200 mg/kg of body weight per day as compound (I) for oral administration or about 10 to 100 mg/kg of body weight per day as compound (I) for parenteral administration.

Furthermore, the compounds (I) and salts thereof have antiviral and antimicrobial activities against various viruses and microbes. Since they have low toxicity as mentioned above, they can therefore be used as antiviral agents, antimicrobial agents or disinfectants for the prevention and treatment of viral and bacterial infectious diseases in warm-blooded animals, especially in mammals (e.g. mouse, rat, cat, dog, rabbit, human).

In using the compounds (I) or salts thereof as microbicides or disinfectants, the compounds (I) or salts thereof may be incorporated into water, an aqueous solution such as isotonic glucose solution or Ringer solution, or a nonaqueous medium such as a vegetable fatty oil (e.g. cotton seed, peanut, corn or sesame oil) in a concentration of about 0.5 to 500 mg/ml. The liquid preparation can be applied to the hand, foot, ear and other parts of mammals for sterilization and disinfection of the application sites.

The compounds (I) or salts thereof can also be used orally in the form of tablets containing about 0.5 to 500 mg thereof together with excipients such as lactose, starch or talc in the prevention and treatment of viral and bacterial infectious diseases in mammals. In that case, the dose is 10 to 200 mg/kg of body weight per day on the compound (I) basis.

The compound (II), which is a starting material in practicing the method of the invention, can be produced, for example, according to the reaction processes shown below.

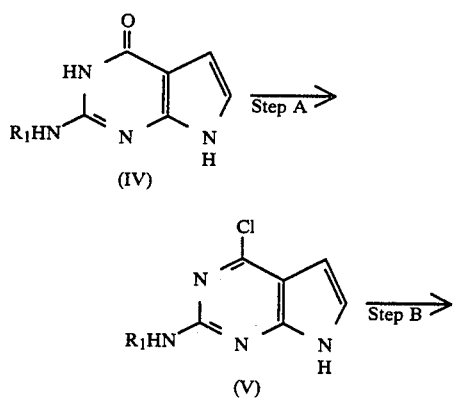

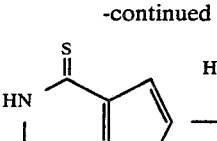

In Step A, the compound (IV) can be converted to the reaction product (V) by reacting with a chlorinating agent (e.g. thionyl chloride, phosphorus oxychloride, phosphorus pentachloride, oxalyl chloride, phthaloyl chloride) in a compound (IV)/chlorinating agent molar ratio of about 1 to 100 in the absence or presence of an appropriate solvent at about 50° C. to 150° C. for about 30 minutes to about 10 hours.

As the solvent usable in the above reaction, there may be mentioned benzene, toluene, xylene, methylene chloride, chloroform, carbon tetrachloride, 1,2-dichloroethane, 1,1,2-trichloroethane, 1,1,2,2-tetrachloroethane and acetonitrile, among others.

When dimethylaniline, diethylaniline, triethylamine, dimethylformamide or the like is added, the above reaction may possibly be carried out under relatively mild conditions.

The thionation in Step B can be effected by bringing the compound (V) into contact with a thionating agent (e.g. hydrogen sulfide, sodium sulfide, thiourea) in a compound (V)/thionating agent molar ratio of about 1 to 1/20 in an inert solvent, generally at about 20° C., to 150° C., for about 30 minutes to one day. Usable solvents are water, alcohols (e.g. methanol, ethanol, propanol, butanol, sec-butanol, tert-butanol, ethylene glycol, methoxyethanol ethoxyethanol), ethers (e.g. dimethyl ether, diethyl ether, tetrahydrofuran, dioxane, monoglyme, diglyme), halogenated hydrocarbons (e.g. dichloromethane, chloroform, carbon tetrachloride), acetonitrile, dimethylformamide, and adequate mixtures of these.

The compound (II) can be produced by condensation of the compound (VI) with the compound (VII) in the presence of formaldehyde or an equivalent thereto (Step C).

The compound (VI) and compound (VII) may be used in a salt form. Such salt may be of the same kind as mentioned hereinabove with respect to the mineral acid salt or organic acid salt of the compound (I).

Said equivalent to formaldehyde includes reagents capable of behaving as an formaldehyde equivalent in the Mannich reaction, such as paraformaldehyde, formalin, methylal, ethylal, piperidinomethylphthalimide and hexamethylenetetramine.

In Step D, the compound (II) can be produced by reacting the compound (VI) with the compound (VII) in a (VII)/(VI) molar ratio of about 1 to 50 in the absence or presence of an appropriate solvent at a temperature of from about 20° C. to the boiling point of the solvent used, preferably within the range of about 20° to 100° C., for about 10 minutes to about 48 hours and then treating the reaction mixture with an acid.

Usable solvents include water, methanol, ethanol, propanol, butanol, pentanol, tetrahydrofuran, dioxane, acetonitrile, pyridine, dimethylformamide, dimethyl sulfoxide, sulfolane, and adequate mixtures of these. The rate of reaction and the yield can be increased by adjusting the reactant mixture to an optimal pH (generally about 2 to 10) with an acid (e.g. hydrochloric acid, sulfuric acid, phosphoric acid, boric acid, acetic acid, oxalic acid, tartaric acid, trifluoroacetic acid, methanesulfonic acid, benzenesulfonic acid, p-toluenesulfonic acid, camphorsulfonic acid), a base (e.g. sodium hydroxide, potassium hydroxide, lithium hydroxide, barium hydroxide, ammonia, triethylamine) or a salt (e.g. sodium chloride, calcium chloride, sodium carbonate, potassium carbonate, sodium hydrogen carbonate, ammonium chloride). As the acid to be used in the final acid treatment, there may be mentioned, for instance, hydrochloric acid, sulfuric acid, nitric acid, phosphoric acid, boric acid, acetic acid, oxalic acid, tartaric acid, trifluoroacetic acid, methanesulfonic acid, benzenesulfonic acid and p-toluenesulfonic acid. The compound (II) can be isolated from the reaction mixture in an adequate manner by any or any combination of usual separation and/or purification methods, such as concentration, solvent extraction, recrystallization and chromatography.

When the compound (II) obtained in this way is in the free form, it may be converted to a salt form by the conventional method for use as a starting compound in practicing the method of the invention.

The salt of compound (II) includes those salt forms as mentioned hereinabove with respect to the compound (I).

In practicing the method of the invention, the compound (III) may be used in the form of a salt. The salt of compound (III) includes those salts as mentioned hereinabove with respect to the compound (IV) and compound (VII).

The following experimental, reference and working examples are further illustrative of this invention.

EXPERIMENTAL EXAMPLE 1

The uptake of compound of Example 1 into tRNA

[$^3$H]-Guanine labeled tRNA(*) (8000 cpm), 70 mM of tris hydrochloride, 60 mM of magnesium chloride, 0.5 unit of rat liver tRNA-guanine transglycosylase and 0.02 OD$_{260}$ of the compound of Example 1 (which appears hereinafter) (100 μl) were incubated at 37° C. for 17 hours. The reaction mixture was applied to a Whatman 3 MM filter paper (Whatman Co., U.S.A.) and washed 3 times with a 5% aqueous solution of trichloroacetic acid and, then, once each with ethanol/ether (1:1) and ether alone. After drying, the uptake of the test compound was determined in a toluenic scintillation fluid. It was found that the compound of Example 1 had been taken up in 81% of tRNA.

(*)tRNA with the firstletter (base) of its anticodon labeled with [$^3$H]guanine.

EXPERIMENTAL EXAMPLE 2

The uptake of the compound of Example 2 into tRNA was determined in the same manner as Experimental Example 1. The result was 57%.

EXPERIMENTAL EXAMPLE 3

$1 \times 10^4$ L5178Y mouse tumor cells were suspended in 2 ml of a RPMI-1640 medium containing 10% of bovine fetal serum, 20 μM of 2-mercaptoethanol and 100 μg/ml kanamycin (Nissui Pharmaceutical Co., Ltd. Japan), and incubated at 37° C. for 24 hours before addition of the drug. Using the above culture fluid as a diluent, the compound of Example 1 was diluted ¼-fold in a series of 5 stages, the maximum concentration of the compound in the medium being 200 μg/ml. The dilutions were further incubated for 72 hours, at the end of which time the cells were counted and the $IC_{50}$ (50% growth inhibitory concentration) was calculated with the count for the non-treated control group being taken as 100%. The $IC_{50}$ value was 22 μg/ml.

EXPERIMENTAL EXAMPLE 4

$5 \times 10^4$ Meth A tumor cells were subcutaneously transplanted into a BALB/c mouse weighing 20 g and starting on the 4th day after transplantation, a solution of the compound of Example 1 in 0.1 ml of distilled water was intraperitoneally injected into the mouse once daily in a dose of 100 mg/kg for 14 consecutive days. On the 35th day after transplantation, the tumor node was enucleated and weighed. Comparison of the weight with that of the non-treated control group showed an inhibition of tumor growth. The tumor growth inhibition rate was 71%.

REFERENCE EXAMPLE 1

Production of
2-amino-4-chloropyrrolo[2,3-d]pyrimidine

2-Aminopyrrolo[2,3-d]pyrimidin-4-one (45 g) was suspended in phosphorus oxychloride (150 ml) and the suspension was stirred at 110° C. for 3 hours. The excess amount of phosphorus oxychloride was distilled off under reduced pressure and ice water (600 ml) was added to the residue, whereby the residue was thoroughly dissolved. The solution was cooled with stirring and adjusted to pH 9 with concentrated aqueous ammonia. The resulting precipitate was collected by filtration, washed with water and recrystallized from hot methanol (4 l) to give the above-identified compound (34.6 g).

NMR(DMSO-$d_6$, 60 MHz): δ 6.23(d, 1H), 6.40(bs, 3H), 7.05 (d, 1H)

IR(KBr): ν 3420, 3330, 3170, 2970, 2820, 1680, 1640, 1620, 1570 cm$^{-1}$

UV $\nu_{max}^{MeOH}$: 232, 258, 319 nm

REFERENCE EXAMPLE 2

Production of
4-chloro-2-n-octanoylaminopyrrolo[2,3-d]pyrimidine

2-Amino-4-chloropyrrolo[2,3-d]pyrimidine (16.9 g) as obtained in Reference Example 1 was suspended and dissolved in dry pyridine (200 ml). With ice-cooling, n-octanoyl chloride (21.2 g) was added to the solution, and the temperature was returned to room temperature. The reaction was allowed to proceed for an hour. To the reaction mixture was added 9.9% ethanolic ammonia (w/v) and the mixture was allowed to stand at room temperature for 2 hours. The solvent was then distilled off under reduced pressure and water (500 ml) was added to the residue. The mixture was stirred at room temperature for an hour and the insoluble matter was collected by filtration, washed with sodium hydrogen carbonate and water, and dried to give a yellow crystalline powder (23.3 g). This product was recrystallized from 1,2-dimethoxyethane to give the above-identified compound (20.9 g).

NMR(CDCl$_3$/DMSO-$d_6$, 60 MHz): δ 0.87(t, 3H), 1.30(bs, 10H), 2.50(t, 2H), 6.43(d, 1H), 7.30(d, 1H), 10.37(s, 1H), 12.10(bs, 1H)

IR(KBr): ν 3430, 3220, 2920, 1645, 1610, 1585, 1375 cm$^{-1}$

REFERENCE EXAMPLE 3

Production of
2-n-octanoylaminopyrrolo[2,3-d]pyrimidine-4-thione

4-Chloro-2-n-octanoylaminopyrrolo[2,3-d]pyrimidine (19.9 g) as obtained in Reference Example 2 and thiourea (38 g) were suspended and dissolved in 2-methoxyethanol (240 ml). The solution was stirred at 100° C. for 25 hours. The solvent was then distilled off under reduced pressure and 1.8% aqueous sodium hydrogen carbonate (300 ml) was added to the residue. The mixture was stirred thoroughly at room temperature and the resulting precipitate was collected by filtration and recrystallized from ethanol to give the above-identified compound (15.7 g).

NMR(CDCl$_3$/DMSO-$d_6$, 60 MHz): δ 0.87(t, 3H), 1.33(bs, 10H), 1.47(t, 2H), 6.63(q, 1H), 6.90(q, 1H), 11.27(bs, 2H), 13.20(bs, 1H)

IR(KBr): ν 3220, 1680, 1635, 1600, 1310 cm$^{-1}$

REFERENCE EXAMPLE 4

Production of
5-N,N-dibenzylaminomethyl-2-octanoylaminopyrrolo[2,3-d]pyrimidine-4-thione 2-Octanoylaminopyrrolo[2,3-d]pyrimidine-4-thione (3.5 g) as obtained in Reference Example 3 and dibenzylamine (9.5 g) were dissolved in water/acetic acid (1:4, 120 ml), and 35% formalin (4.2 g) was added to the solution. The reaction was allowed to proceed at 60° C. for 14 hours. The solvent was then distilled off under reduced pressure and water (30 ml) was added, followed by further distillation. 2N-HCl (64 ml) and methanol (100 ml) were added to the residue and the mixture was stirred at 60° C. for 1.5 hours. The methanol was mostly distilled off under reduced pressure and the aqueous layer was made alkaline with ammonia, followed by addition of sodium acid sulfite (5.7 g). The mixture was extracted with chloroform and the chloroform layer was concentrated to dryness to give the above-identified compound (crude, 3.95 g). This product can be submitted to the next reaction step directly without further purification.

NMR(CDCl$_3$, 60 MHz): δ 0.83(t, 3H), 1.20(bs, 10H), 2.70(t, 2H), 4.07(bs, 4H), 4.40(bs, 2H), 7.20(m, 11H)

REFERENCE EXAMPLE 5

Production of
5-N,N-diisobutylaminomethyl-2-octanoylaminopyrrolo[2,3-d]pyrimidine-4-thione 2-Octanoylaminopyrrolo[2,3-d]pyrimidine-4-thione (3.5 g) was reacted with diisobutylamine (4.5 g) in the same manner as Reference Example 4 to give the above-identified compound (crude, 2.3 g).

NMR(CDCl$_3$, 60 MHz): δ 0.85(t, 3H), 0.90(d, 12H), 1.20–2.00(m, 12H), 2.40–2.70(m, 6H), 4.40(bs, 2H), 7.20(bs, 1H)

EXAMPLE 1

Production of 2-amino-5-[(3S,4R,5S)-4,5-dihydroxycyclopent-1-en-3-ylaminomethy-]pyrrolo[2,3-d]pyrimidine-4-thione (6-thio Q base)

The crude 5-N,N-dibenzylaminomethyl-2-octanoylaminopyrrolo[2,3-d]pyrimidine-4-thione (3.3 g) as obtained in Reference Example 4 and (3S,4R,5S)-4,5-O-isopropylidene-4,5-dihydroxycyclopent-1-en-3-ylamine (1.55 g) were dissolved in ethanol (150 ml) and the reaction was allowed to proceed in a sealed tube at 75° C. for 20 hours. After cooling, tetrahydrofuran (75 ml) and then a 40% aqueous solution of potassium hydroxide (11 ml) were added to the reaction mixture and the resulting mixture was allowed to stand at 5° C. for 3 days followed by addition of a 30% aqueous solution of ammonium chloride (11 ml). The mixture was concentrated to dryness and the residue was separated and purified by silica gel column chromatography using ethanol/chloroform (1:4) containing 7% $NH_3$ as the eluent to give 2-amino-5-[(3S,4R,5S)-4,5-O-isopropylidene-4,5-dihydroxycyclopent-1-en-3-ylaminomethyl]-pyrrolo[2,3-d]pyrimidine-4-thione. The whole amount of this product was dissolved in methanol (100 ml) and 2N—HCl (16 ml) and the solution was allowed to stand at room temperature overnight and then concentrated to dryness to give the above-identified compound in the dihydrochloride form (1.07 g).

NMR($D_2O$, 60 MHz): δ 4.20–4.60(m, 2H), 4.47(bs, 2H), 6.13(m, 2H), 7.03(s, 1H),

IR(KBr): ν 2930, 2780, 1690, 1590, 1200 cm$^{-1}$

EXAMPLE 2

Production of 2-amino-5-aminomethylpyrrolo[2,3-d]pyrimidine-4-thione (6-thio Pre Q1 base)

The crude 5-N,N-dibenzylaminomethyl-2-octanoylaminopyrrolo[2,3-d]pyrimidine-4-thione (1.0 g) as obtained in Reference Example 4 was dissolved in a mixture of ethanol (50 ml), tetrahydrofuran (30 ml) and concentrated aqueous ammonia (20 ml) and the reaction was allowed to proceed in a sealed tube at 80° C. for 1.5 hours. The solvent was then distilled off under reduced pressure and the residue was washed with ether. The insoluble matter was separated and purified with the aid of cellulose powder (Avicel, Asahi Chemical Industry Co., Ltd., Japan) using concentrated ammonia-saturated n-butanol as the eluent to give the above-identified compound (215 mg). The physicochemical determinations were made on the hydrochloride obtained by conversion with methanolic hydrochloric acid.

NMR($D_2O$/$CD_3OD$, 60 MHz): δ 4.13(bs, 2H), 6.90(bs, 1H)

IR(KBr): ν 2920, 1690, 1595, 1195 cm$^{-1}$

EXAMPLE 3

Production of 2-amino-5-isoamylaminomethylpyrrolo[2,3-d]pyrimidine-4-thione

The crude 5-N,N-dibenzylaminomethyl-2-n-octanoylaminopyrrolo[2,3-d]pyrimidine-4-thione (2.01 g; 4 milimole) as obtained in Reference Example 4 and isoamylamine (1.75 g; 20 milimole) were dissolved in methanol (200 ml), and the reaction was allowed to proceed at 55° C. for 17 hours under stirring. The reaction mixture was concentrated under reduced pressure, the crystals emerged were recovered and washed with a small amount of methanol and ether and then dried, whereby the product (0.89 g) was obtained.

NMR(DMSO-$d_6$, 90 MHz): δ 0.83(d, 6H), 1.03–1.60(m, 3H), 2.28(t, 2H), 3.70(s, 2H), 6.63(s, 1H)

IR(KBr): ν 3350, 3200, 3100, 2960 1600, 1540, 1460, 1320, 1240, 1200, 1025, 945 cm$^{-1}$

EXAMPLE 4

In a similar manner to that of Example 3, the crude 5-N,N-dibenzylaminomethyl-2-n-octanoylaminopyrrolo[2,3-d]pyrimidine-4-thione (4 milimole) is reacted with an amine [Compound (III), 20 milimole], whereby the following 7-deazapurine derivatives [Compound (I)] were obtained.

It should be noted that, in the physico-chemical properties, the data of NMR are those measured at 90 MHz employing DMSO-$d_6$ as a solvent, and the data of IR are those measured by employing KBr as a solvent.

(1) Product:
2-Amino-5-(2-hydroxybenzylaminomethyl)pyrrolo[2,3-d]pyrimidine-4-thione Yield: 1.07 (g)
Properties:
NMR: δ 3.80(s, 2H), 3.83(s, 2H), 6.70 (s, 1H), 6.60–6.75(m, 2H), 6.95–7.17(m, 2H),
IR: ν 3200, 1620, 1595, 1565, 1460, 1380, 1250, 1020 cm$^{-1}$
Compound (III):

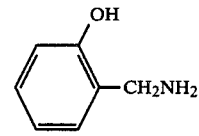

(2) Product:
2-Amino-5-cyclopentylaminomethylpyrrolo[2,3-d]pyrimidine-4-thione

Yield: 0.99 (g)
Properties:
NMR: δ 1.20–1.83(m, 8H), 2.84–3.13(m, 1H), 3.73(s, 2H), 6.67(s, 1H)
IR: ν 3180, 1640, 1590, 1560, 1535, 1490, 1360 cm$^{-1}$
Compound (III):

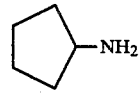

(3) Product:
2-Amino-5-[2-(2-hydroxyethoxy)ethylaminomethyl]-pyrrolo[2,3-d]pyrimidine-4-thione Yield: 0.47 g
Properties:
NMR: δ 2.57(t, 2H) 3.30–3.56(m, 6H), 3.77(s, 2H), 6.67(s, 1H)
IR: ν 3200, 2950, 1640, 1590, 1540, 1480, 1390 cm$^{-1}$
Compound (III):

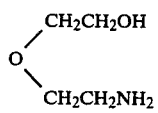

(4) Product:
2-Amino-5-piperidinomethylpyrrolo[2,3-d]pyrimidine-4-thione

Yield 0.58 (g)
Properties:
NMR: δ 1.43(s, 6H), 2.33–2.50(s, 4H), 3.87(s, 2H), 6.63(s, 1H)
IR: ν 3150, 2950, 1620, 1590, 1535, 1460, 1240, 1020 cm$^{-1}$
Compound (III):

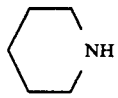

(5) Product:
2-Amino-5-allylaminomethylpyrrolo[2,3-d]pyrimidine-4-thione

Yield: 57 (g)
Properties:
NMR: δ 3.10(d, 2H), 3.76(s, 2H), 4.93–5.27 (m, 2H), 5.63–6.07(m, 1H), 6.68(s, 1H)
IR: ν 3200, 1630, 1590, 1540, 1465, 1240, 1020 cm$^{-1}$
Compound (III): $CH_2=CHCH_2NH_2$ (6) Product:
2-Amino-5-[2-(2-aminoethylaminomethyl)ethylaminomethyl]pyrrolo[2,3-d]pyrimidine-4-thione Yield: 0.40 (g)
Properties:
NMR: δ 2.57(s, 8H) 3.80(s, 2H), 6.70(s, 1H)
IR: ν 3300, 2920, 1590, 1535, 1465, 1235, 1020 cm$^{-1}$
Compound (III):

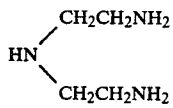

(7) Product:
2-Amino-5-phenylaminomethylpyrrolo[2,3-d]pyrimidine-4-thione

Yield: 0.67 (g)
Properties:
NMR: δ 4.40(s, 2H), 6.73(s, 1H), 6.47–6.63 (m, 3H), 6.93–7.10(m, 2H)
IR: ν 3320, 1625, 1600, 1565, 1440, 1385, 1200 cm$^{-1}$
Compound (III):

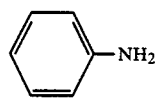

(8) Product:
2-Amino-5-(2-hydroxyphenylaminomethyl)pyrrolo2,3-d]pyrimidine-4-thione Yield: 0.31 (g)
Properties:
NMR: δ 4.42(s, 2H), 6.27–6.70(m 4H) 6.75(d, 1H)
IR: ν 3340, 1625, 1595, 1565, 1440, 1200, 965 cm$^{-1}$
Compound (III):

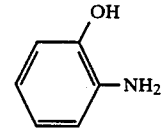

(9) Product:
2-Amino-5-tert-butoxycarbonylmethylaminomethyl-pyrrolo[2,3-d]pyrimidine-4-thione Yield: 0.54 (g)
Properties:
NMR: δ 1.37(s, 9H), 3.13(s, 2H), 3.82(s, 2H), 6.68(s, 1H)
IR: ν 3350, 3150, 1730, 1650, 1560, 1365, 1235 cm$^{-1}$
Compound (III):

What we claim is:
1. A 7-deazapurine compound of the formula:

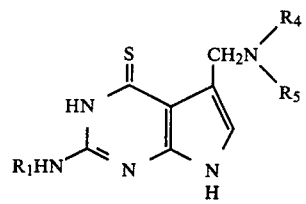

wherein
$R_1$ is a hydrogen atom, an alkanoyl group of up to 18 carbon atoms, benzoyl, toluoyl or naphthoyl group and $R_4$ and $R_5$ each is a hydrogen atom or a hydrocarbon residue of the class consisting of $C_{1-18}$-alkyl, $C_{2-12}$-alkenyl, $C_{3-12}$-cycloalkyl, $C_{3-8}$-cycloalkenyl, benzyl, α-methylbenzyl, phenethyl, diphenylmethyl, phenyl and naphthyl residues, which hydrocarbon radicals may optionally be mono-, di- or tri-substituted with $C_{1-4}$-alkyl, $C_{1-4}$-alkoxy, hydroxy-$C_{1-4}$-alkoxy, $C_{1-4}$-alkanoyl, $C_{1-4}$-alkanoyloxy, $C_{2-4}$-alkoxycarbonyl, halo, hydroxy, nitro, cyano, trifluoromethyl, amino, $C_{1-4}$-monoalkylamino, carboxymethylamino, di-($C_{1-4}$-alkyl)amino, dicarboxymethylamino and $C_{1-4}$alkanoylamino groups or wherein $R_4$ and $R_5$, together with the adjacent nitrogen atom, form a cyclic amino group of the class consisting of azetidinyl, pyrrolidinyl, pyrrolinyl, pyrrolyl, imidazolyl, pyrazolyl, imidazolinyl, piperidino, morpholino, dihydropyridyl, tetrahydropyridyl, N-methylpiperazinyl, N-ethylpiperazinyl, azacycloheptyl, azacyclooctyl, isoindolyl, indolyl, indolinyl, 2-isoindolinyl, azacyclononyl and azacyclodecyl groups and pharmaceutically acceptable salts thereof.

2. A compound as claimed in claim 1, wherein $R_1$ is hydrogen.

3. A compound as claimed in claim 1, wherein $R_4$ and $R_5$ are hydrogen atoms.

4. A compound as claimed in claim 1, wherein $R_4$ is hydrogen and $R_5$ is a hydrocarbon residue having the molecular weight of not more than about 400.

5. A compound as claimed in claim 7, wherein the hydrocarbon residue is an alkyl group of 1 to 18 carbon atoms which may be substituted.

6. A compound as claimed in claim 1, wherein the hydrocarbon residue is benzyl.

7. A compound as claimed in claim 1, wherein the hydrocarbon residue is a cycloalkyl group of 3 to 12 carbon atoms which may be substituted.

8. A compound as claimed in claim 1, wherein $R_4$ and $R_5$, together with the adjacent nitrogen atom, form a cyclic amino group of 4- to 10-membered ring which may be substituted.

9. A compound as claimed in claim 1, wherein $R_1$ is hydrogen, $R_4$ is hydrogen and $R_5$ is (3S,4R,5S)-4,5-dihydroxycyclopent-1-en-3-yl.

10. A compound as claimed in claim 1, wherein $R_1$ is hydrogen, $R_4$ is hydrogen and $R_5$ is hydrogen.

11. A compound as claimed in claim 1, wherein $R_1$ is hydrogen, $R_4$ is hydrogen and $R_5$ is 2-hydroxyphenyl.

12. A compound as claimed in claim 1, wherein $R_1$ is hydrogen, $R_4$ is hydrogen and $R_5$ is cyclopentyl.

13. A compound as claimed in claim 1, wherein $R_1$ is hydrogen, $R_4$ is hydrogen and $R_5$ is phenyl.

14. A compound as claimed in claim 1, wherein $R_1$ is hydrogen, $R_4$ is hydrogen and $R_5$ is tert-butoxycarbonylmethyl.

15. A compound as claimed in claim 1, wherein $R_1$ is hydrogen, $R_4$ is hydrogen and $R_5$ is allyl.

16. A compound as claimed in claim 1, wherein $R_1$ is hydrogen and $R_4$ and $R_5$, taken together with the adjacent nitrogen atom, form piperidino group.

17. A compound as claimed in claim 1 wherein $R_1$ is an alkanoyl group of up to 18 carbon atoms.

* * * * *